(12) United States Patent
Duncan

(10) Patent No.: US 9,737,135 B2
(45) Date of Patent: Aug. 22, 2017

(54) ORAL CARE IMPLEMENT

(71) Applicant: COLGATE-PALMOLIVE COMPANY, New York, NY (US)

(72) Inventor: Kelly Gail Duncan, Washington, NJ (US)

(73) Assignee: COLGATE-PALMOLIVE COMPANY, New York, NY (US)

(*) Notice: Subject to any disclaimer, the term of this patent is extended or adjusted under 35 U.S.C. 154(b) by 0 days.

(21) Appl. No.: 15/038,033

(22) PCT Filed: Nov. 20, 2013

(86) PCT No.: PCT/US2013/071001
§ 371 (c)(1),
(2) Date: May 19, 2016

(87) PCT Pub. No.: WO2015/076796
PCT Pub. Date: May 28, 2015

(65) Prior Publication Data
US 2016/0278513 A1 Sep. 29, 2016

(51) Int. Cl.
*A46B 11/04* (2006.01)
*A46B 13/04* (2006.01)
(Continued)

(52) U.S. Cl.
CPC ............... *A46B 13/04* (2013.01); *A46B 9/04* (2013.01); *A46B 11/0086* (2013.01);
(Continued)

(58) Field of Classification Search
CPC ............ A46B 11/0086; A46B 11/0062; A46B 11/0065; A46B 2200/1066
See application file for complete search history.

(56) References Cited

U.S. PATENT DOCUMENTS 4,275,750 A 6/1981 Clark
4,388,011 A 6/1983 Smith
(Continued)

FOREIGN PATENT DOCUMENTS

CN 202698207 1/2013
DE 8911487 11/1989
(Continued)

OTHER PUBLICATIONS

International Search Report and the Written Opinion of the International Searching Authority issued in International Patent Application PCT/US2013/071001 mailed Jul. 29, 2014.

*Primary Examiner* — Jennifer C Chiang

(57) ABSTRACT

An oral care implement having an applicator and a cover member. In one aspect, the invention is an oral care implement comprising: a handle body extending along a longitudinal axis from a distal end to a proximal end; an applicator at the proximal end of the handle body, the applicator fluidly coupled to a reservoir containing an oral care material; a cover member having a cap portion, the cap portion comprising a resilient valve that is self-biased into a closed state so as to enclose the applicator; and wherein relative positioning between the applicator and the cover member can be altered between: (1) a storage state in which the cap portion of the cover member encloses the applicator and the resilient valve is in the closed state; and (2) an application state in which the applicator extends through the resilient valve and the resilient valve is in an open state.

20 Claims, 4 Drawing Sheets

(51) Int. Cl.
*A46B 9/04* (2006.01)
*A61C 17/22* (2006.01)
*A46B 5/00* (2006.01)
*A46B 11/00* (2006.01)

(52) U.S. Cl.
CPC .......... *A61C 17/227* (2013.01); *A46B 5/0016* (2013.01); *A46B 11/0062* (2013.01); *A46B 11/0065* (2013.01); *A46B 2200/1066* (2013.01)

(56) References Cited

U.S. PATENT DOCUMENTS

| | | |
|---|---|---|
| 5,967,152 A | 10/1999 | Rimkus |
| 6,012,863 A | 1/2000 | Sakurai |
| 6,015,293 A | 1/2000 | Rimkus |
| 6,220,773 B1 | 4/2001 | Wiegner et al. |
| 6,290,417 B1 | 9/2001 | Kaminski |
| 6,554,516 B1 | 4/2003 | Christopher |
| 6,554,526 B1 | 4/2003 | Christopher |
| 6,957,467 B2 | 10/2005 | Cabedo-Deslierres et al. |
| 7,309,185 B2 | 12/2007 | Thorpe et al. |
| 7,478,452 B2 | 1/2009 | Rosenblood et al. |
| 8,511,323 B2 | 8/2013 | Jimenez et al. |
| 9,603,444 B2 * | 3/2017 | Boyd .................. A46B 11/001 |
| 2004/0240928 A1 | 12/2004 | Trocino |
| 2006/0133885 A1 | 6/2006 | Kaminski |
| 2011/0135379 A1 | 6/2011 | Jimenez et al. |
| 2011/0308030 A1 | 12/2011 | Jimenez et al. |
| 2011/0318085 A1 | 12/2011 | Alcocer |
| 2016/0331121 A1 * | 11/2016 | Moskovich ............ A46B 9/045 |

FOREIGN PATENT DOCUMENTS

| | | |
|---|---|---|
| DE | 9309004 | 8/1993 |
| FR | 1223650 | 6/1960 |
| WO | WO 2007/010476 | 1/2007 |

* cited by examiner

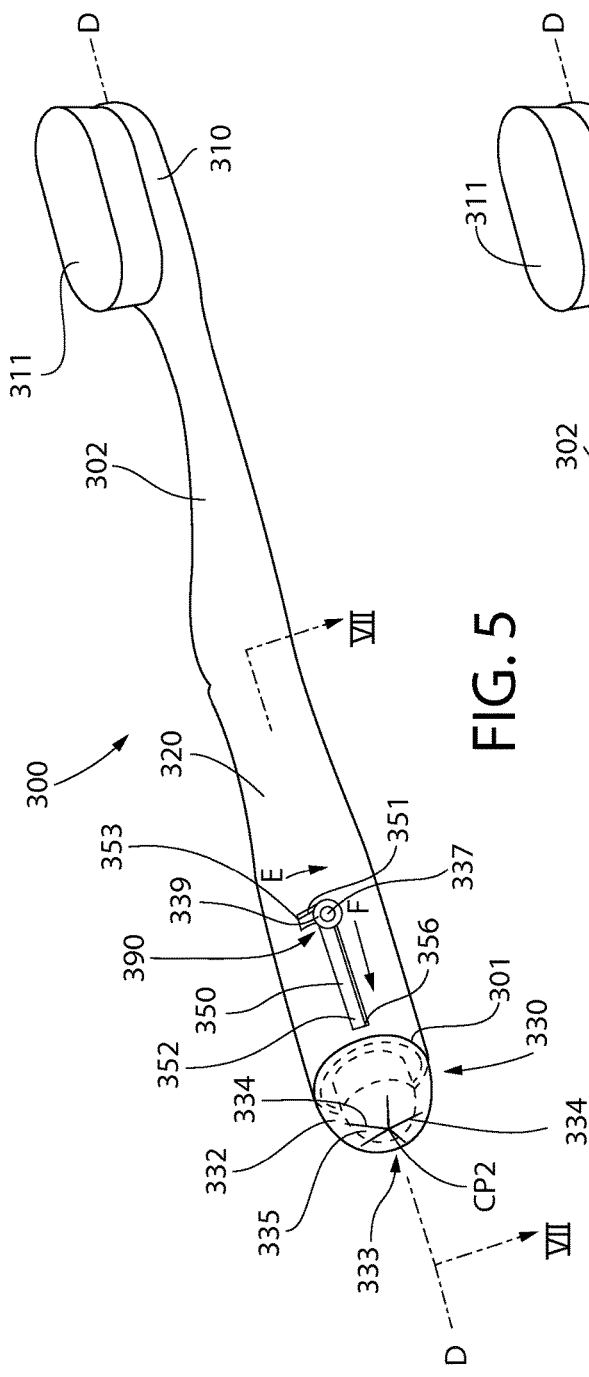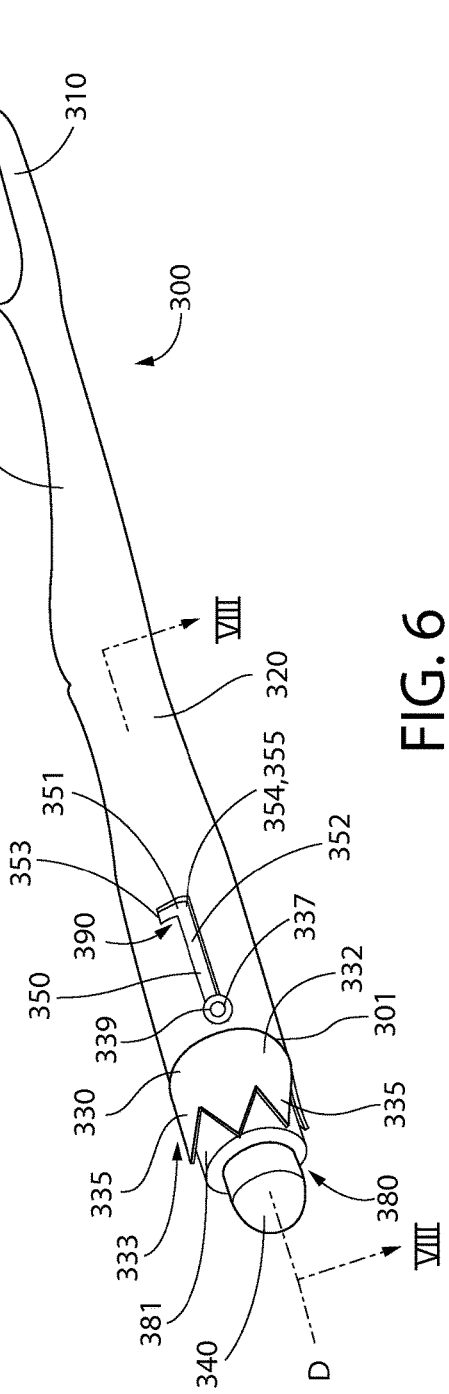
FIG. 5
FIG. 6

ORAL CARE IMPLEMENT

BACKGROUND

Oral care implements such as toothbrushes that include dentifrice or other oral care materials in the handle so that the toothbrush and dentifrice can be carried as a single unit are known. However, in typical such devices the dentifrice/oral care material dispenser must be completely removed from the handle of the toothbrush in order to apply the dentifrice onto the bristles or directly onto a user's teeth and/or gums. Using such conventional devices, a user may forget to place the dispenser back into the handle of the toothbrush, which may result in the dispenser getting misplaced and rendering that particular toothbrush useless. Thus, a need exists for an oral care implement including an oral care material that minimizes the likelihood of misplacing the dispenser while also protecting an applicator of the dispenser against damage.

BRIEF SUMMARY

Exemplary embodiments according to the present disclosure are directed to an oral care implement comprising a handle body, an applicator at a proximal end of the handle body that is fluidly coupled to a reservoir and a cover member. Relative positioning between the applicator and the cover member can be altered between a storage state in which the cover member encloses the applicator and an application state in which the applicator extends through the cover member.

In one aspect, the invention can be an oral care implement comprising: a handle body extending along a longitudinal axis from a distal end to a proximal end, a reservoir located within the handle body, the reservoir containing an oral care material; an applicator protruding from the proximal end of the handle body, the applicator fluidly coupled to the reservoir to dispense the oral care material; a cover member comprising a cap portion, the cap portion comprising a resilient valve that is self-biased into a closed state; and the cover member movably coupled to the handle body so as to be alterable between: (1) an extended position in which the cap portion of the cover member encloses the applicator and the resilient valve is in the closed state; and (2) a retracted position in which the applicator extends through the resilient valve and the resilient valve is in an open state.

In another aspect, the invention can be an oral care implement comprising: a handle body extending along a longitudinal axis from a distal end to a proximal end, a cavity formed into the handle body; an oral care dispenser comprising a housing having a reservoir for containing an oral care material and an applicator fluidly coupled to the reservoir; a cover member comprising a cap portion coupled to the proximal end of the handle body, the cap portion comprising a resilient valve that is self-biased into a closed state; and wherein the oral care dispenser is at least partially disposed within the cavity of the handle body, the oral care dispenser movably coupled to the handle body so as to be alterable between: (1) a retracted position in which the cap portion of the cover member encloses the applicator and the resilient valve is in the closed state; and (2) an extended position in which the applicator of the oral care dispenser extends through the resilient valve and the resilient valve is in an open state.

In yet another aspect, the invention can be an oral care implement comprising: a handle body extending along a longitudinal axis from a distal end to a proximal end; an applicator at the proximal end of the handle body, the applicator fluidly coupled to a reservoir containing an oral care material; a cover member having a cap portion, the cap portion comprising a resilient valve that is self-biased into a closed state so as to enclose the applicator; and wherein relative positioning between the applicator and the cover member can be altered between: (1) a storage state in which the cap portion of the cover member encloses the applicator and the resilient valve is in the closed state; and (2) an application state in which the applicator extends through the resilient valve and the resilient valve is in an open state.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 5 is a front perspective schematic view of an oral care implement having a cover member and a movable oral care dispenser in accordance with a second embodiment of the present invention, wherein the oral care dispenser is in a retracted position;

FIG. 6 is a front perspective schematic view of the oral care implement of FIG. 5A wherein the oral care dispenser is in an extended position;

DETAILED DESCRIPTION

Figure 1:
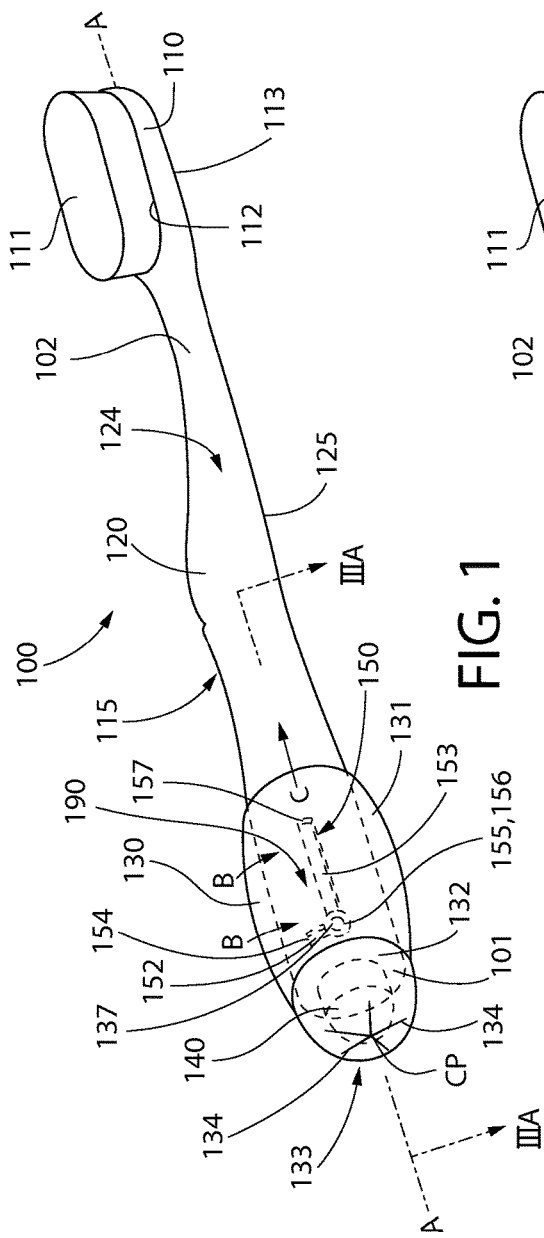
FIG. 1 is front perspective schematic view of an oral care implement having an applicator and a movable cover member in accordance with a first embodiment of the present invention, wherein the cover member is in an extended position.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom"

as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
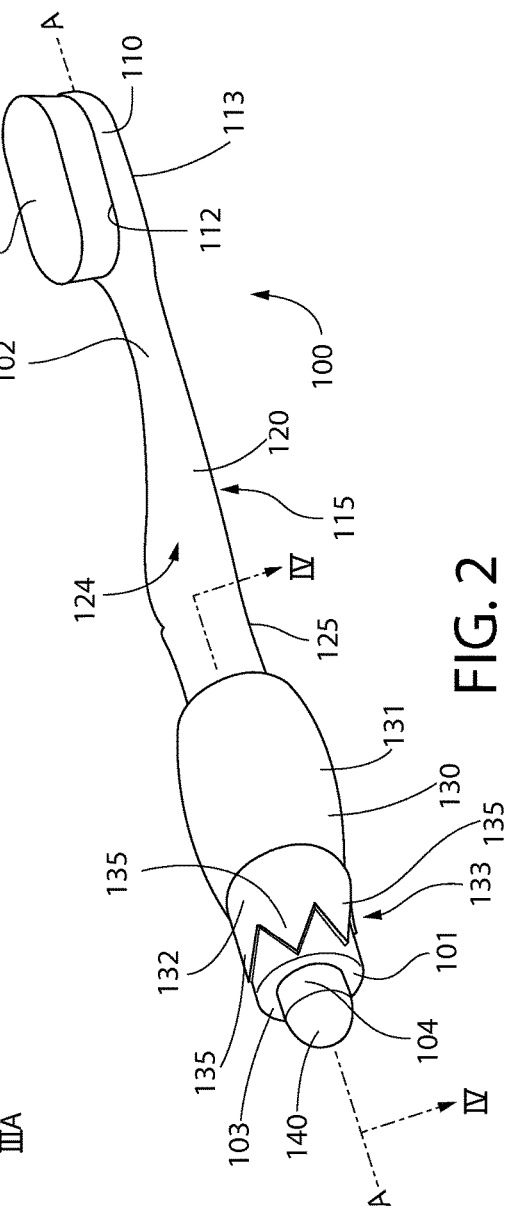
FIG. 2 is a front perspective schematic view of the oral care implement of FIG. 1 wherein the cover member is in a retracted position.

Referring first to FIGS. 1 and 2 concurrently, an oral care implement 100 is illustrated in accordance with an embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement 100 generally includes a head 110 and a handle 115. The handle 115 generally comprises a handle body 120 and a cover member 130 that is movably coupled to the handle body 120. The handle body 120 extends along a longitudinal axis A-A from a proximal end 101 to a distal end 102. Conceptually, the longitudinal axis A-A is a reference line that is generally coextensive with the three-dimensional center line of the handle body 120 and the head 110. Because the handle body 120 may, in certain embodiments, be a non-linear structure, the longitudinal axis A-A of the handle body 120 may also be non-linear in certain embodiments. However, the invention is not to be so limited in all embodiments and in certain other embodiments the handle body 120 may have a simple linear arrangement and thus a substantially linear longitudinal axis A-A.

The handle body 120 is an elongated structure that provides the mechanism by which the user can hold and manipulate the oral care implement 100 during use. The handle body 120 comprises a front surface 124 and an opposing rear surface 125. In the exemplified embodiment, the handle body 120 is generically depicted having various contours for user comfort. Of course, the invention is not to be so limited in all embodiments and in certain other embodiments the handle body 120 can take on a wide variety of shapes, contours and configurations, none of which are limiting of the present invention unless so specified in the claims.

In the exemplified embodiment, the handle body 120 is formed of a rigid plastic material, such as for example without limitation polymers and copolymers of ethylene, propylene, butadiene, vinyl compounds and polyesters such as polyethylene terephthalate. Of course, the invention is not to be so limited in all embodiments and the handle body 120 may include a resilient material, such as a thermoplastic elastomer, as a grip cover that is molded over portions of or the entirety of the handle body 120 to enhance the gripability of the handle 120 during use. For example, portions of the handle body 120 that are typically gripped by a user's palm during use may be overmolded with a thermoplastic elastomer or other resilient material to further increase comfort to a user.

The head 110 of the oral care implement 100 is coupled to the handle body 120 and comprises a front surface 112 and an opposing rear surface 113. In the exemplified embodiment, the head 110 is formed integrally with the handle body 120 as a single unitary structure using a molding, milling, machining or other suitable process. However, in other embodiments the handle body 120 and the head 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. The head 110 may be formed of any one of the materials discussed above with regard to the handle body 120.

In the exemplified embodiment, the head 110 of the oral care implement 100 is provided with a plurality of tooth cleaning elements 111 extending from the front surface 112. In the exemplified embodiments, the tooth cleaning elements 111 are generically illustrated as a block. In certain embodiments the exact structure, pattern, orientation and material of the tooth cleaning elements 111 are not to be limiting of the present invention. Thus, as used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 111 of the present invention can be connected to the head 110 in any manner known in the art. For example, staples/anchors, in-mold tufting (IMT) or anchor free tufting (AFT) could be used to mount the cleaning elements/tooth engaging elements. In certain embodiments, the invention can be practiced with various combinations of stapled, IMT or AFT bristles. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

Although not illustrated herein, in certain embodiments the head 110 may also include a soft tissue cleanser coupled to or positioned on its rear surface 113. An example of a suitable soft tissue cleanser that may be used with the present invention and positioned on the rear surface of the head 110 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implement 100 may not include any soft tissue cleanser.

Referring to FIGS. 1-4 concurrently, the oral care implement 100 will be further described. The oral care implement 100 comprises an applicator 140 protruding from the proximal end 101 of the handle body 120. In the exemplified embodiment, the applicator 140 is fixedly secured to the handle body 120 so as to always be extending or protruding from the proximal end 101 of the handle body 120. Of course, the applicator 140 may be removably secured to the handle body 120 in other embodiments. Regardless of whether or not the applicator 140 is removable, the applicator 140 protrudes or extends from the proximal end 101 of the handle body 120 when the applicator 140 is coupled to the handle body 120.

As will be discussed in more detail below, the applicator 140 may be formed of a rubber material (i.e., a thermoplastic elastomer), a capillary material, a porous material, a metal, a rigid plastic material or any other desired material. Furthermore, in the exemplified embodiment a reservoir 122 is located within the handle body 120. More specifically, the interior of the handle body 120 is hollow, and thus an inner surface 121 of the handle body 120 defines the reservoir 122. However, the invention is not to be so limited in all embodiments and in certain other embodiments the reservoir may be formed in a separate cartridge or housing that is positioned within the handle body 120. In the exemplified embodiment, the reservoir 122 contains an oral care material 123 and the applicator 140 is fluidly coupled to the reservoir 122 so that the oral care material 123 contained within the reservoir 122 can be dispensed to a user's oral cavity through the applicator 140. The length of the handle body 120 that is hollow to form the reservoir 122 can be made as desired to contain a desired amount of the oral care material 123 therein. Thus, in certain embodiments only a proximal portion of the handle body 120 is hollow, and in other embodiments the entirety of the handle body 120 is hollow from the proximal end 101 to the distal end 102.

The oral care material 123 can be any type of material that is desired to be applied to a user's oral cavity including the teeth and gums. Thus, the oral care material 123 may be a dentifrice, or it may be an active agent such as a tooth whitening agent. Any suitable tooth whitening agent can be used in the present invention, including without limitation peroxide containing tooth whitening compositions. While a tooth whitening agent is one of the preferred active agents in the present invention, other active agents can be used with the invention and, thus, stored within the reservoir 122. Contemplated active agents include without limitation, anti-bacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. In certain embodiments, the active agent is free of (i.e., is not) toothpaste. Instead, in such embodiments the active agent is intended to provide benefits in addition to merely brushing one's teeth. However, other suitable oral care agents could include lip balm or other materials that are typically available in a semi-solid state.

As noted above, in certain embodiments the applicator 140 may be formed of a rubber or elastomeric material, such as for example without limitation a thermoplastic elastomer, in order to comfortably apply the oral care material 123 directly onto the user's teeth and/or gums without damaging the user's teeth and/or gums. Of course, the invention is not to be so limited and in other embodiments the applicator 140 may be formed of other materials, including without limitation metals, plastics or capillary materials. In the embodiment depicted in FIGS. 3A and 4, the applicator 140 has a rounded, spherical, or half-circle shape. Of course, the invention is not to be so limited in all embodiments and other shapes are possible as desired (see FIG. 3B, discussed below). In embodiments whereby the applicator 140 is formed of a thermoplastic elastomer, the applicator 140 may include a dispensing orifice 141 extending therethrough to enable the oral care material 123 to pass through the applicator 140 for application onto the user's teeth and/or gums. The dispensing orifice 141 may be a self-sealing opening that only opens in response to user pressure or the oral care implement 100 may include a plug in order to seal the dispensing orifice 141 until application of the oral care material 123 to the user's oral cavity is desired.

Figure 3A:
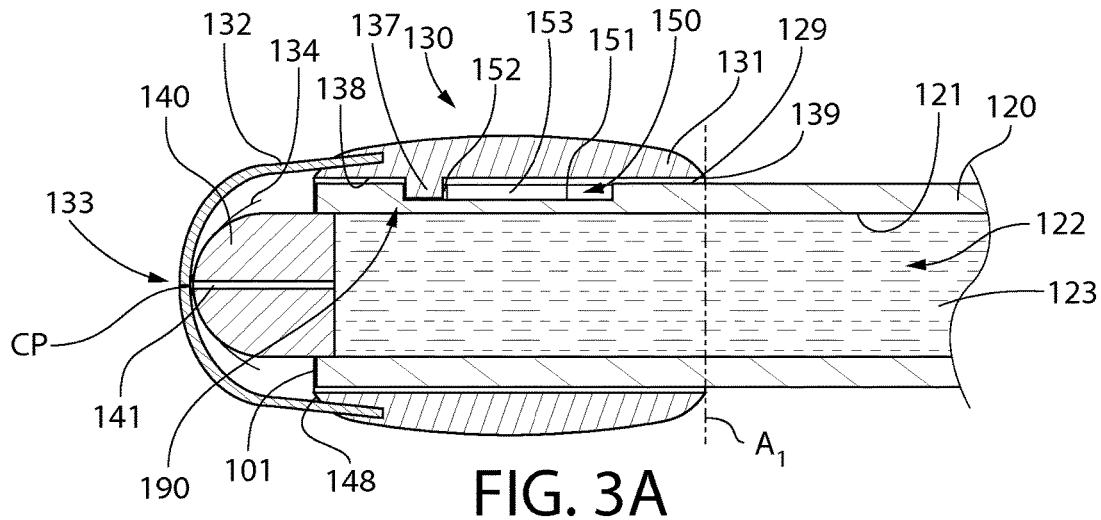
FIG. 3A is a cross-sectional view taken along line IIIA-IIIA in FIG. 1.
Figure 3B:
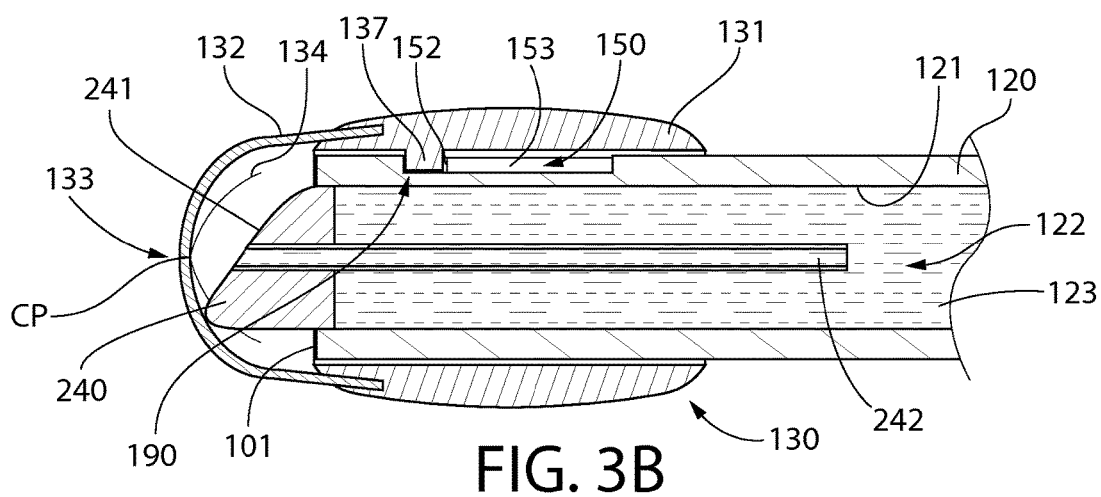
FIG. 3B is a cross-sectional view taken along line IIIA-IIIA in FIG. 1 in accordance with an alternative embodiment of the present invention.

In the embodiment depicted in FIG. 3B, an alternative embodiment of an applicator 240 is illustrated having a dispensing end 241. In FIG. 3B, the dispensing end 241 of the applicator 240 is angled in order to allow for efficient scraping of a user's teeth during application of the oral care material 123 thereon. Specifically, the oral care material 123 can be applied to a user's teeth via the applicator 240, and then the dispensing end 241 of the applicator 240 can be moved along the tooth to spread the oral care material 123 thereon. Furthermore, the applicator 240 is coupled to a tube 242, which may be formed of a capillary material or may simply be a plastic tube having a passageway therethrough to carry the oral care material 123 from the reservoir 122 to the applicator 240. During use, the oral care material 123 travels through the tube 242 from the reservoir 122 and through the applicator 240 for application to a user's oral cavity. The applicator 240 may be formed from any of the materials discussed above with regard to the applicator 140.

In certain embodiments as noted above the applicator 140 can be formed of a capillary material, such as a sponge, a ceramic, a porous plastic or any other material that is capable of wicking the oral care material 123 from the reservoir 122 onto the applicator 140 via capillary action. In such embodiments the reservoir 122 may include a wick therein to facilitate transfer of the oral care material 123 from the reservoir 122 onto the applicator 140, or direct contact between the applicator 140 and the oral care material 123 contained within the reservoir 122 may enable such fluid transfer. In still other embodiments, the applicator 140 may be coupled to the proximal end 101 of the handle body 120 so as to be capable of rotating 360° in all directions relative to the handle body 120. As a result, a portion of the applicator 140 can dip into the oral care material 123 within the reservoir 122 and then continue to rotate so that the portion of the applicator 140 that dipped into (and is coated by) the oral care material 123 is positioned external to the reservoir 122 for application to a user's oral cavity. Any of a number of different shapes can be used for the applicator 140, and the applicator 140 can be coupled to the handle body 120 in any desired manner that is capable of dispensing the oral care material 123 from the reservoir 122 to the applicator 140 and to a user's oral cavity. Thus, in certain embodiments the applicator 140 is fluidly coupled to the reservoir 122 to dispense the oral care material 123 regardless of the manner in which the applicator 140 is coupled to the reservoir 122.

In the exemplified embodiment, the proximal end 101 of the handle body 120 forms a shoulder 103, and a connector 104 extends from the shoulder 103. In this embodiment, the applicator 140 is disposed within the connector 104, which may be an annular or ring-like structure having an opening sized, shaped and configured to retain the applicator 140 therein. In other embodiments, the applicator 140 may be coupled directly to the proximal end 101 of the handle body 120.

As noted above, the handle 115 comprises the handle body 120 and the cover member 130. In FIG. 1, the cover member 130 is illustrated as being see-through so that the features on the handle body 120 that are beneath the cover member 130 as well as internal features of the cover member 130 are visible for ease of understanding. However, it should be appreciated that the cover member 130 may be transparent, translucent, opaque, colored, white or the like as desired. The cover member 130 generally comprises a base portion 131 and a cap portion 132. In certain embodiments, the base portion 131 of the cover member 130 may be formed of a rigid material, such as a hard plastic, and the cap portion 132 of the cover member 130 may be formed of a resilient material, such as a thermoplastic elastomer. However, the invention is not to be so limited in all embodiments and the base portion 131 and the cap portion 132 may both be formed of the same material (either a resilient material or a rigid material) in other embodiments.

The cap portion 132 of the cover member 130 comprises a resilient valve 133 that is self-biased into a closed state, as illustrated in FIGS. 1, 3A and 3B. More specifically, a plurality of slits 134 (only some of which are denoted with a reference numeral to avoid clutter) are formed into the cap portion 132 of the cover member 130 and extend radially from a central point CP and towards the base portion 131 of the cover member 130. In the exemplified embodiment, there are five slits in the shape of a starfish, although more or less than five slits are possible in other embodiments. In the exemplified embodiment, the plurality of slits 134 do not extend the entire length of the cap portion 132 of the cover member 130 from the central point CP to the base portion 131 of the cover member 130. Rather, the plurality of slits 134 extend between approximately ¼ to ¾ of the length of the cap portion 132 from the central point CP to the base portion 131, more specifically approximately ⅓ to ⅔ of the length of the cap portion 132 from the central point CP to the base portion 131, still more preferably approximately ⅓ to ½ of the length of the cap portion 132 from the central point CP to the base portion 131, and even more specifically approximately ½ of the length of the cap portion 132 from the central point CP to the base portion 131. Of course, in certain other embodiments the slits 134 may extend the entire length of the cap portion 132 of the cover member 130 if desired. The plurality of slits 134 create a plurality of flaps 135 in the cap portion 132 of the cover member 130. The plurality of slits 134 and the plurality of flaps 135 collectively form the resilient valve 133. The resilient valve 133 is self-biased into the closed state due to the flaps 135 converging towards each other at all times, the resilient valve 133 being in the closed state when no intervening structure (such as the handle body 120) blocks the flaps 135 from converging into abutting contact with one another as discussed in more detail below.

Figure 4:
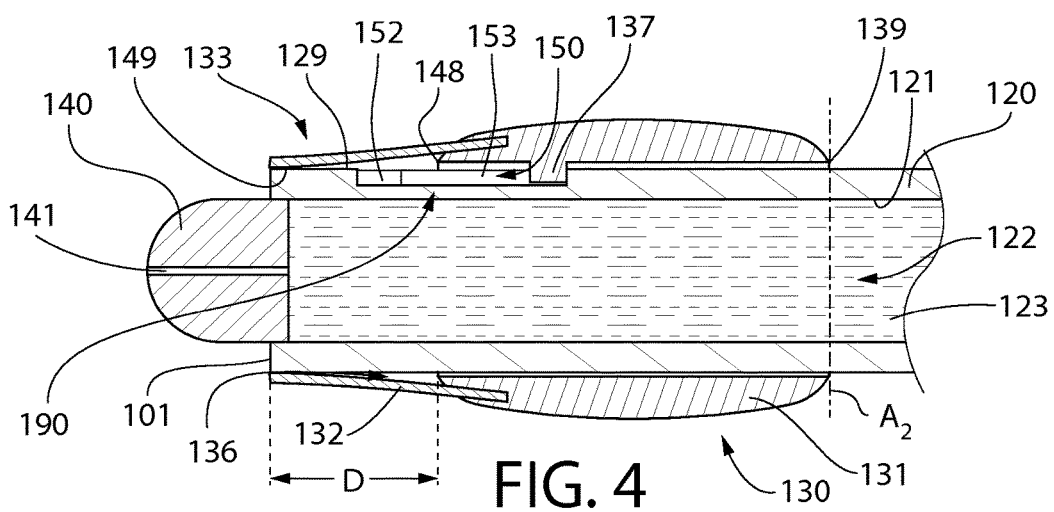
FIG. 4 is a cross-sectional view taken along line IV-IV in FIG. 2.
Figure 7:
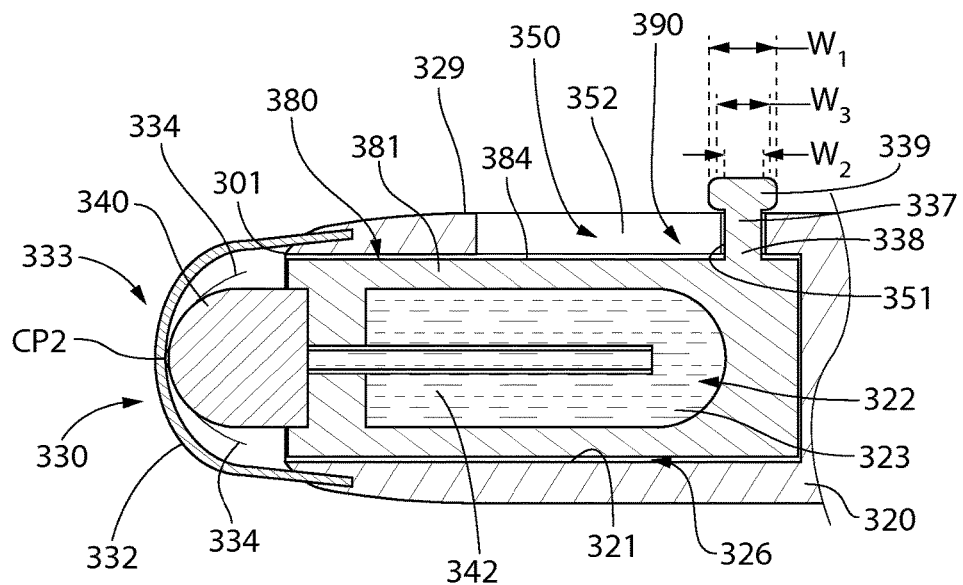
FIG. 7 is a cross-sectional view taken along line VII-VII in FIG. 5.
Figure 8:
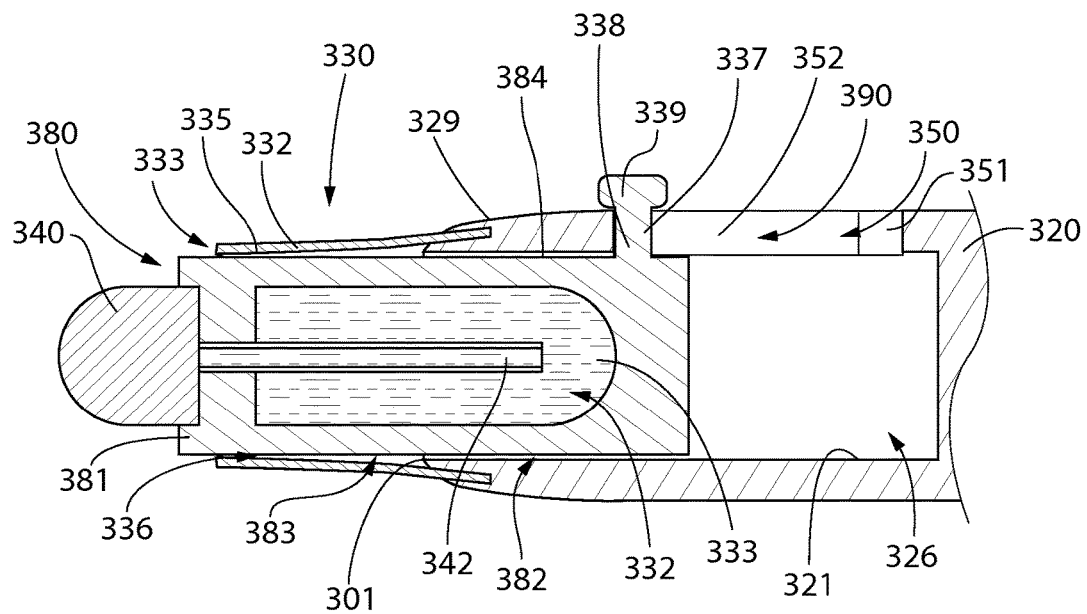
FIG. 8 is a cross-sectional view taken along line VIII-VIII in FIG. 6.

As noted above the cover member 130 is movably coupled to the handle body 120 so as to be alterable between an extended position illustrated in FIGS. 1, 3A and 3B and a retracted position illustrated in FIGS. 2 and 4. When the cover member 130 is in the extended position, the cap portion 132 of the cover member 130 encloses the applicator 140 and the resilient valve 133 is in the closed state because the flaps 135 converge into abutting contact with one another. When the cover member 130 is in the retracted position, the applicator 140 extends or protrudes through the resilient valve 133 and the resilient valve 133 is in the open state. Specifically, when the cover member 130 alters from the extended position to the retracted position, the applicator 140 and the proximal end 101 of the handle body 120 push on the resilient valve 133 and force the flaps 135 to separate along the slits 134, thereby forming a passageway 136 through the resilient valve 133 (and through the cap portion 132 of the cover member 130) through which the applicator 140 extends. When the cover member 130 alters from the retracted position back to the extended position, the flaps 135 again converge towards one another so as to be in abutting contact due to their self-bias in order to re-close the resilient valve 133. Thus, any time that the cover member 130 is in the extended position, the resilient valve 133 is in the closed state so that the applicator 140 is protected against damage and the applicator 140 is not exposed for oral care use. Furthermore, any time that the cover member 130 is in the retracted position, the resilient valve 133 is in the open state so that the applicator 140 extends through the resilient valve 133 and is exposed for oral care use. Thus, when the cover member 130 is in the retracted position, the applicator 140 can be used to apply the oral care material 123 to a user's oral care surfaces.

As discussed above, the cover member 130 is movably coupled to the handle body 120 so as to be alterable between the extended and retracted positions. Thus, the oral care implement 100 includes an attachment feature 190 that couples the cover member 130 to the handle body 120 while enabling the cover member 130 to move relative to the handle body 120. Specifically, in the exemplified embodiment the attachment feature 190 comprises a channel 150 formed into an outer surface 129 of the handle body 120 and a protuberance 137 extending from an inner surface 138 of the cover member 130. Of course, the invention is not to be so limited and in other embodiments the attachment feature 190 can be a channel formed into the inner surface 138 of the cover member 130 and a protuberance extending from the outer surface 129 of the handle body 120. Furthermore, any other mechanism for movably coupling the cover member 1320 to the handle body 120 can be used in other embodiments including an elevator/screw mechanism, frictional fit between the outer surface 129 of the handle body 120 and the inner surface 138 of the cover member 130, or the like.

In the exemplified embodiment, the channel 150 is defined by a pair of sidewalls and a floor 151. In the exemplified embodiment, the channel 150 is an L-shaped channel having a first portion 152 that extends in a direction substantially transverse to the longitudinal axis A-A and a second portion 153 that extends in a direction substantially parallel to or axial with the longitudinal axis A-A. Thus, in the exemplified embodiment the first and second portions 152, 153 of the channel 150 are substantially perpendicular to one another. However, the invention is not to be so limited and in certain other embodiments the first and second portions 152, 153 of the channel 150 can be oriented at any of various angles relative to one another other than being perpendicular. Furthermore, in certain embodiments the channel may only include the second portion 153 while omitting the first portion 152. However, including the first and second portions 152, 153 of the channel 150 and making the channel 150 L-shaped (or similar) results in the creation of a locking feature that prevents the cover member 130 from being easily altered from the extended position to the retracted position, as discussed in more detail below.

The first portion 152 of the channel 150 extends from a first end 154 to a second end 155 and the second portion 153 of the channel 150 extends from a first end 156 to a second end 157. In the exemplified embodiment, the second end 155 of the first portion 152 of the channel 150 and the first end 156 of the second portion 153 of the channel 150 are located at an intersection between the first and second portions 152, 153 of the channel 150. More specifically, the second end 155 of the first portion 152 of the channel 150 and the first end 156 of the second portion 153 of the channel 150 at the same location in the channel 150.

Furthermore, as discussed above in the exemplified embodiment the attachment feature 190 further includes the protuberance 137 extending from the inner surface 138 of the base portion 131 of the cover member 130. The protuberance 137 is positioned within the channel 150 to movably couple the cover member 130 to the handle body 120 while preventing the cover member 130 from being separated from the handle body 120. Specifically, the protuberance 137 is permitted to freely slide within the channel 150 as discussed in more detail below, but cannot be removed from the channel 150 due to a combination of the interaction between the sidewalls of the channel 150 and the protuberance 137 as well as the interaction between the outer surface 129 of the handle body 120 and the inner surface 138 of the cover member 130. In certain embodiments, the protuberance 137 may have a width that is slightly smaller than the width of the channel 150 so that friction between the protuberance 137 and the sidewalls of the channel 150 prevent the protuberance 137 from freely sliding within the channel 150 when no force is applied to the cover member 130. Thus, in response to user force that exceeds the friction between the protuberance 137 and the sidewalls of the channel 150, the protuberance 137 can slide within the channel 150 to alter the cover member 130 between the extended and retracted positions, as discussed in more detail below.

As noted above, in certain embodiments the base portion 131 of the cover member 130 is formed of a rigid plastic material while the cap portion 132 of the cover member 130 is formed of a resilient material. The protuberance 137 may be formed integrally with the base portion 131 of the cover member 130. Forming the base portion 131 of the cover member 130 (and also the protuberance 137) out of a rigid plastic material facilitates maintaining the protuberance 137 within the channel 150 to maintain the coupled relationship between the cover member 130 and the handle body 120. However, the invention is not to be so limited in all embodiments and in certain other embodiments the base portion 131 of the cover member 130 and/or the protuberance 137 may be formed out of a resilient material if desired.

In the exemplified embodiment, when the cover member 130 is in the extended position, the protuberance 137 is positioned within the first portion 152 of the channel 150. Furthermore, when the cover member 130 is in the retracted position, the protuberance 137 is positioned within the second portion 153 of the channel 150. In its locked position, the cover member 130 is in the extended position and the protuberance 137 is positioned at the first end 154 of the first portion 152 of the channel 150. In order to move the cover member 130 from the locked and extended position to the retracted position, first the cover member 130 is rotated about the longitudinal axis A-A (in the direction of the arrows B depicted in FIG. 1) so that the protuberance 137 slides within the first portion 152 of the channel 150 from the first end 154 of the first portion 152 of the channel 150 to the second end 155 of the first portion 152 of the channel 150. Upon reaching the second end 155 of the first portion 152 of the channel 150, the cover member 130 can then be translated axially in the direction of the longitudinal axis A-A (i.e., in the direction of the arrow C depicted in FIG. 1) so that the protuberance 137 slides within the second portion 153 of the channel 150 from the first end 156 of the second portion 153 of the channel 150 to the second end 157 of the second portion 153 of the channel 150. When the protuberance 137 is located at the second end 157 of the second portion 153 of the channel 150, the cover member 130 is in the retracted position, the applicator 140 extends through the resilient valve 133 of the cover member 130 and the applicator 140 is exposed for oral care use. In certain embodiments, the applicator 140 may protrude/extend through the resilient valve 133 of the cover member 130 when the protuberance 137 is located between the first and second ends 156, 157 of the second portion 153 of the channel 150 and continue to extend further through the resilient valve 133 as the protuberance 137 continues to be slide towards the second end 156 of the second portion 153 of the channel 150.

Thus, using the technique described above, the cover member 130 is both rotationally and translationally coupled to the handle body 120. Furthermore, in the exemplified embodiment both rotational and translational movement of the cover member 130 relative to the handle body 120 is required in order to alter the cover member 130 from the extended position to the retracted position and vice versa. This serves as a built-in locking feature because the cover member 130 cannot be moved into the retracted position until the protuberance 137 is located at the second end 155 of the first portion 152 of the channel 150 because only the second end 155 of the first portion 152 of the channel 150 is aligned with the second portion 153 of the channel 150.

Although the L-shape is described above as being the locking feature, in other embodiments the protuberance 137 may include a retractable extension that is biased into contact with the sidewalls or floor 151 of the channel 150 to enhance the frictional contact between the protuberance 137 and the sidewalls or floor 151 of the channel 150 to prevent the cover member 130 from being easily moved. Additionally, the sidewalls or floor 151 of the channel 150 may include a recess or indent into which the retractable extension of the protuberance 137 may nest when it is desired to lock the cover member 130 in place. In such an embodiment, the cover member 130 may include a depressible button that upon being depressed causes the retractable extension to retract so that the protuberance 137 is spaced from the sidewalls and/or floor 151 of the channel 150 (or is removed from the recess in the sidewalls or floor 151 of the channel 150) to enable the cover member 130 to freely move relative to the handle body 120. In another embodiment, the retractable extension may extend from the sidewalls of the channel 150 into the channel 150 to prevent movement of the cover member 130 relative to the handle body 120 (i.e., to lock the protuberance 137 at a certain location, such as at the first end 154 of the first portion 152 of the channel 150). Of course, any other type of locking feature can be used as desired to prevent the cover member 130 from being altered from the extended position into the retracted position until desired so that the cover member 130 can protect the applicator 140 against damage during periods of non-use.

As can be seen from the above, the cover member 130 is coupled to the handle body 120 in both the extended and retracted positions. Furthermore, the applicator 140 is also coupled to the handle body 120 when the cover member 130 is in both the extended and retracted positions. When the cover member 130 is in the extended position, a distal end 139 of the base portion 131 of the cover member 130 is located at a first axial location $A_1$ of the handle body 120 and a proximal end 148 of the base portion 131 of the cover member 130 is substantially transversely aligned with the proximal end 101 of the handle body 120 (substantially aligned being anything from an exact alignment to an offset in the alignment of approximately 3 mm). When the cover member 130 is in the retracted position, the distal end 139 of the base portion 131 of the cover member 130 is located at a second axial location $A_2$ of the handle body 120 and the proximal end 148 of the base portion 131 of the cover member 130 is spaced a distance D from the proximal end 101 of the handle body 120. The second axial location $A_2$ is closer to the distal end 102 of the handle body 120 (and also closer to the head 110) than the first axial location $A_1$. Thus, the cover member 130 does not need to be fully separated from the handle body 120 in order to use the applicator 140 to dispense the oral care material 123. Rather, merely translating or sliding the cover member 130 about the handle body 120 towards the head 110 (and towards the distal end 102 of the handle body 120) while the cover member 130 remains coupled to the handle body 120 (due to the protuberance 137 being positioned within the channel 150) alters the cover member 130 between the extended and retracted positions.

In the exemplified embodiment described above, the channel 150 is formed into the handle body 120 and the protuberance 137 extends from the cover member 130. However, as noted above the invention is not to be so limited and in certain other embodiments the channel may be formed into the cover member 130 and the protuberance may extend from the handle body 120. In such an embodiment, the protuberance of the handle body 120 would be positioned within the channel of the cover member 130 to couple the cover member 130 to the handle body 120. This would achieve the same functional result as has been discussed above with regard to the movement of the cover member 130 relative to the handle body 120.

Referring briefly to FIGS. 1 and 3A, the oral care implement 100 is illustrated with the cover member 130 in the extended position. When the cover member 130 is in the extended position 130, the base portion 131 of the cover member 130 substantially circumferentially surrounds the handle body 120 while the cap portion 132 of the cover member 130 substantially circumferentially surrounds the applicator 140. Referring now to FIGS. 2 and 4, the oral care implement is illustrated with the cover member 130 in the retracted position. When the cover member 130 is in the retracted position, both the cap portion 132 and the base portion 131 of the cover member 130 substantially circumferentially surround the handle body 120 and no portion of the cover member 130 surrounds the applicator 140. As a result, when the cover member 130 is in the retracted position the applicator is completely exposed for oral care application. However, the invention is not to be so limited and in certain embodiments a portion of the cap portion 132 of the cover member 130 will surround a portion of the applicator 140 when the cover member is in the retracted position.

Furthermore, when the cover member 130 is in the retracted position, at least a portion of an inner surface 149 of the cap portion 132 of the cover member 130 is in surface contact with the outer surface 129 of the handle body 120. This occurs due to the self-biasing of the resilient valve 133 of the cap portion 132 of the cover member 130. Specifically, the flaps 135 of the cap portion 132 of the cover member 130 are continuously pulling inwardly towards the handle body 120 (and towards one another) in order to close the resilient valve 133 when the cover member 130 is in the extended position. As a result, contact between the resilient valve 133 (i.e., the flaps 135) and the handle body 120 occurs when the cover member 130 is in the retracted position.

Referring now to FIGS. 5 and 6 concurrently, an oral care implement 300 will be described in accordance with another embodiment of the present invention. The oral care implement 300 is similar to the oral care implement 100 in many respects. Features of the oral care implement 300 that are similar to features of the oral care implement 100 will be similarly numbered except that the 300-series of numbers will be used. Furthermore, certain features of the oral care implement 300 will not be described herein in the interest of brevity, it being understood that the description of the similar feature from the oral care implement 100 applies. If a feature of the oral care implement 300 is numbered but not described, the description of the similar feature of the oral care implement 100 applies.

The oral care implement 300 comprises a handle 315 and a head 310, the head having a plurality of tooth cleaning elements 311 extending therefrom. The handle 315 generally comprises a handle body 320 and a cover member 330. The handle body 320 extends along a longitudinal axis D-D from a proximal end 301 to a distal end 302. The materials of the handle body 320 and the head 310 can be any of the materials as have been described above with reference to the oral care implement 100. The oral care implement 300 further comprises an applicator 340 protruding from the proximal end 301 of the handle body 320. However, unlike the oral care implement 100, the applicator 340 is formed as a part of an oral care dispenser 380 that is housed within a cavity of the handle body 320. Furthermore, differently from the oral care implement 100, in the oral care implement 300 the oral care dispenser 380 is movable relative to the handle body 120 and the cover member 330 is fixed or non-movable relative to the handle body 120.

Specifically, referring to FIGS. 5-8 concurrently, the handle body 320 comprises an inner surface 321 that forms a cavity 326 and an outer surface 329. The oral care dispenser 380 is at least partially disposed within the cavity 326 of the handle body 320. The oral care dispenser 380 comprises a housing 381 and the applicator 340, the housing 381 having a reservoir 322 for containing an oral care material 323 therein. The applicator 340 is fluidly coupled to the reservoir 322 in any manner desired, such as any one of the structural embodiments discussed above. Specifically, in the exemplified embodiment the applicator 340 is fluidly coupled to the reservoir 322 and to the oral care material 323 via a tube 342, which can either be a hollow tube having a passageway therethrough or a capillary tube. Thus, the applicator 340 may also be formed of a capillary material so that the oral care material 323 can be dispensed to the applicator 340 via capillary action, or the applicator 340 may be formed of rubber, plastic or the like and have a passageway therethrough for the dispensing of the oral care material 323. The oral care material 323 can be any type of oral care material as discussed above with regard to the oral care material 123.

The oral care implement 300 further comprises the cover member 330 coupled to the proximal end 301 of the handle body 320. The cover member 330 comprises a cap portion 332, and the cap portion 332 comprises a resilient valve 333 that is self-biased into a closed state (see FIGS. 5 and 7). The resilient valve 333 can be altered from the closed state to an open state (see FIGS. 6 and 8) in a manner that will be discussed in more detail below. In the exemplified embodiment, the cover member 330 is directly and fixedly coupled to the proximal end 301 of the handle body 320 such that the cover member 330 is not movable relative to the handle body 320 (other than the resilient valve 333 altering between the closed and open states More specifically, the cover member 330 does not move axially or rotationally relative to the handle body 320 The resilient valve 333 is self-biased into the closed state to form a dome or enclosure that surrounds the applicator 340 of the oral care dispenser 380. As will be discussed in more detail below, in the oral care implement 300 it is the oral care dispenser 380 that is movable and alterable between a retracted position in which the cap portion 332 of the cover member 330 encloses the applicator 340 and the resilient valve 333 is in the closed state and an extended position in which the applicator 340 of the oral care dispenser 380 extends through the resilient valve 333 and the resilient valve 333 is in the open state. Thus, the cover member 330 remains located at and fixedly secured to the proximal end 301 of the handle body 320 at all times regardless of the location of the oral care dispenser 380 and the applicator 340.

The resilient valve 333 is formed by a plurality of slits 334 (only some of which are denoted with a reference numeral to avoid clutter) that are formed into the cap portion 332 of the cover member 330 and extend radially from a central point CP2 and towards the proximal end 301 of the handle body 320. In the exemplified embodiment, there are five slits in the shape of a starfish, although more or less than five slits are possible in other embodiments. In the exemplified embodiment, the plurality of slits 334 do not extend the entire length of the cap portion 332 of the cover member 330 from the central point CP2 to the proximal end 301 of the handle body 320. Rather, the plurality of slits 334 extend between approximately ¼ to ¾ of the length of the cap portion 232 from the central point CP2 to the proximal end 301 of the handle body 320, more specifically approximately ⅓ to ⅔ of the length of the cap portion 332 from the central point CP2 to the proximal end 301 of the handle body 320, still more preferably approximately ⅓ to ½ of the length of the cap portion 332 from the central point CP2 to the proximal end 301 of the handle body 320, and even more specifically approximately ½ of the length of the cap portion 332 from the central point CP2 to the proximal end 301 of the handle body 320. Of course, in certain other embodiments the slits 334 may extend the entire length of the cap portion 332 of the cover member 330 if desired.

The plurality of slits 334 create a plurality of flaps 335 in the cap portion 332 of the cover member 330. The plurality of slits 334 and the plurality of flaps 335 collectively form the resilient valve 333. The resilient valve 333 is self-biased into the closed state due to the flaps 335 converging towards each other at all times, the resilient valve 333 being in the closed state when no intervening structure (such as the housing 381 of the oral care dispenser 380) blocks the flaps 335 from converging into abutting contact with one another as discussed in more detail below. In certain embodiments the entire cover member 330 is formed of a resilient material, such as a thermoplastic elastomer. However, the invention is not to be so limited and in certain other embodiments only the resilient valve 333 is formed of a resilient material and the remainder of the cover member 330 can be formed of any desired material (i.e., hard plastic, metal, etc.). Regardless of the material that forms the cover member 330, the resilient valve 333 is self-biased into the closed state to protect the applicator 340 against potential damage.

As discussed above, the oral care dispenser 380 is positioned within the cavity 326 of the handle body 300. More specifically, in the exemplified embodiment when the oral care dispenser 380 is in the retracted position, the housing 381 of the oral care dispenser 380 is entirely located within the cavity 326 and the applicator 340 of the oral care dispenser 380 extends or protrudes from the proximal end 301 of the handle body 320. However, despite protruding from the proximal end 301 of the handle body 320, the applicator 340 is still protected because it is enclosed by the cap portion 332 of the cover member 330 when the oral care dispenser 380 is in the retracted position. When the oral care dispenser 380 is in the extended position, a distal portion 382 of the housing 381 of the oral care dispenser 380 is located within the cavity 326 while a proximal portion 383 of the housing 381 of the oral care dispenser 380 extends from the proximal end 301 of the handle body 320. Thus, at least a portion of the oral care dispenser 380 remains positioned within the cavity 326 of the handle body 320 in both the retracted and extended positions and at least a portion of the applicator 340 of the oral care dispenser 340 protrudes from the proximal end 301 of the handle body 340 in both the retracted and extended positions. Furthermore, when the oral care dispenser 380 is in the extended position, the applicator 340 protrudes through the cap portion 332 of the cover member 330 and is accessible to apply the oral care material 323 to a user's oral cavity.

When the oral care dispenser 380 moves from the retracted position to the extended position, the applicator 340 and/or the housing 381 of the oral care dispenser 380 contacts the resilient valve 333 and causes the flaps 335 of the resilient valve 333 to separate along the slits 334. As the oral care dispenser 380 continues to move, the flaps 335 continue to separate until a passageway 336 is formed through the resilient valve 333 (i.e., through the cap portion 332 of the cover member 330). The oral care dispenser 380 continues to move until the applicator 340 protrudes through the passageway 336 and is exposed for oral care use.

In the exemplified embodiment, coupling of the oral care dispenser 380 to the handle body 320 is achieved via an attachment feature 390. In the exemplified embodiment, the attachment feature 390 comprises a recess 350 formed through the handle body 320 and a protuberance 337 extending from an outer surface 384 of the housing 381 of the oral care dispenser 380. The recess 350 creates an elongated opening through the handle body 320 through which the protuberance 337 extends to enable a user to move the oral care dispenser 380 between the retracted and extended positions.

In the exemplified embodiment, the recess 350 is L-shaped and comprises a first portion 351 that extends in a direction substantially transverse to the longitudinal axis D-D and a second portion 352 that extends in a direction substantially parallel to the longitudinal axis D-D. In the exemplified embodiment, the L-shaped recess 350 is similar in structure and shape to the L-shaped channel 150 discussed above except that the L-shaped recess 350 extends through the handle body 320 so as to form an opening or passageway whereas the channel 150 is merely a groove formed into the outer surface 129 of the handle body 120. Thus, the first portion 351 of the recess 350 is substantially perpendicular to the second portion 352 of the recess 350, although other arrangements are possible.

In the exemplified embodiment, the housing 381 of the oral care dispenser 380 is positioned within the cavity 326 and the protuberance 327 extends from the outer surface 384 of the housing 381 and into and through the recess 350 in order to movably couple the oral care dispenser 380 to the handle body 320. More specifically, the protuberance 337 comprises a base portion 338 extending from the outer surface 384 of the housing 381 and an annular flange 339 extending from the base portion 338. The base portion 338 of the protuberance 337 is positioned within the recess 350 and the annular flange 339 of the protuberance 337 is located outside of or external to the recess 350, the annular flange 339 of the protuberance 337 being exposed and/or accessible for gripping or sliding by a user's hand or fingers. In the exemplified embodiment, the recess 350 has a first width $W_1$, the base portion 338 of the protuberance 337 has a second width $W_2$ and the annular flange 339 of the protuberance 337 has a third width $W_3$ such that the second width $W_2$ is less than the first width $W_1$ and the third width $W_3$ is greater than the first width $W_1$. This difference in the widths of the various structures enables the protuberance 337 to freely slide and move within the recess 350 while providing a knob-like structure (i.e., the annular flange 339 of the protuberance 337) for the user to grip for moving the oral care dispenser 380.

In certain embodiments, the user may alter positioning of the oral care dispenser 380 simply by pressing one finger against the annular flange 339 of the protuberance 337 because movement of the annular flange 339 results in the same movement by the entire oral care dispenser 380 due to the annular flange 339 being coupled to or integrally formed with the housing 381 of the oral care dispenser. Furthermore, in certain embodiments the protuberance 337 may be removable from the housing 381 of the oral care dispenser 380, such as by attaching the protuberance 337 to the housing 381 of the oral care dispenser 380 with corresponding male and female threaded screws, a tight fit, hook and loop fasteners or the like. In such embodiments, the protuberance 337 can be removed from the housing 381 to enable the entire oral care dispenser 380 to be removed from the cavity 326. This can be desirable in order for the oral care dispenser 380 to be refilled or replaced with a new oral care dispenser when the oral care material 323 stored therein is depleted.

Similar to the discussion of the movement of the cover member 130 above, movement of the oral care dispenser 380 is as follows. When the protuberance 337 is located within the first portion 351 of the recess 350, the oral care dispenser 380 is in the retracted position (see FIGS. 5 and 7). When the oral care dispenser 380 is in the retracted position, the cap portion 332 of the cover member 330 encloses the applicator 340 and the resilient valve 333 is in the closed state. The user can grip the protuberance 337 and rotate it (and the oral care dispenser 380) about the longitudinal axis D-D in the direction of the arrow E from a first end 353 of the first portion 351 of the recess 350 to a second end 354 of the first portion 351 of the recess 350. When the protuberance 337 is located at the second end 354 of the first portion 351 of the recess 350, the protuberance 337 is axially aligned with the second portion 352 of the recess 350. Thus, upon reaching the second end 354 of the first portion 351 of the recess 350, the protuberance is translated axially in the direction of the arrow F from a first end 355 of the second portion 352 of the recess 350 to a second end 356 of the second portion 352 of the recess 350. Upon reaching the second end 356 of the second portion 352 of the recess 350, the oral care dispenser 380 is in the extended position and the applicator 340 of the oral care dispenser 380 extends through the resilient valve 333 and the resilient valve 333 is in the open state (see FIGS. 6 and 8). When the oral care dispenser 380 is in the extended position, a portion of the resilient valve 333 (i.e., the flaps 335) is in surface contact with the outer surface 384 of the housing 381 of the oral care dispenser 380. In altering the oral care dispenser 380 from the retracted position to the extended position, the oral care dispenser 380 in its entirety moves axially in a direction away from the head 310 of the oral care implement 300.

As discussed above, in the exemplified embodiment both a rotational and translational movement of the oral care dispenser 380 achieves movement of the oral care dispenser 380 from the retracted position to the extended position. Of course, the invention is not to be so limited in all embodiments and in certain other embodiments the recess 350 may only include the second portion 352 while omitting the first portion 351 so that only translational/axial movement is required to alter the oral care dispenser 380 from the retracted position to the extended position. Furthermore, in certain embodiments the protuberance 337 and/or the recess 350 may include additional locking features, such as the retractable extensions discussed above with regard to the oral are implement 100.

Furthermore, it should be appreciated that in both the oral care implement 100 and the oral care implement 300, relative positioning between the applicator 140, 340 and the cover member 130, 330 can be altered between: (1) a storage state in which the cap portion 132, 332 of the cover member 130, 430 encloses the applicator 140, 340 and the resilient valve 133, 333 is in the closed state; and (2) an application state in which the applicator 140, 340 extends through the resilient valve 133, 433 and the resilient valve 133, 333 is in the open state. Thus, the movement of either one of the cover member 130 or the oral care dispenser 380 can be used to alter the relative positioning between the applicator 140, 340 and the cover member 130, 330 between the storage and application states.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
a handle body extending along a longitudinal axis from a proximal end to a distal end, a reservoir located within the handle body, the reservoir containing an oral care material;
an applicator protruding from the proximal end of the handle body, the applicator fluidly coupled to the reservoir to dispense the oral care material;
a cover member comprising a cap portion, the cap portion comprising a resilient valve that is self-biased into a closed state; and
the cover member movably coupled to the handle body so as to be alterable between: (1) an extended position in which the cap portion of the cover member encloses the applicator and the resilient valve is in the closed state; and (2) a retracted position in which the applicator extends through the resilient valve and the resilient valve is in an open state.

2. The oral care implement according to claim 1 further comprising a plurality of slits formed into the cap portion of the cover member and extending radially from a central point, the plurality of slits creating a plurality of flaps in the cap portion of the cover member, the plurality of slits and the plurality of flaps collectively forming the resilient valve.

3. The oral care implement according to claim 2 wherein when the cover member is in the extended position the resilient valve is self-biased into the closed state and adjacent flaps abut one another, and wherein when the cover member is in the retracted position the plurality of flaps separate along the plurality of slits thereby forming a passageway through the cap portion of the cover member through which the applicator extends.

4. The oral care implement according to claim 1 wherein the cover member further comprises a base portion, and wherein when the cover member is in the extended position the base portion of the cover member surrounds the handle body and the cap portion of the cover member surrounds the applicator and when the cover member is in the retracted position the cap portion and the base portion of the cover member surround the handle body.

5. The oral care implement according to claim 1 further comprising:
a channel formed into the handle body; and
a protuberance extending from an inner surface of the cover member, the protuberance positioned within the channel to movably couple the cover member to the handle body.

6. The oral care implement according to claim 1 wherein the cover member is coupled to the handle body in both the extended and retracted positions.

7. The oral care implement according to claim 1 further comprising:
a channel formed into the cover member; and
a protuberance extending from an outer surface of the handle body, the protuberance of the handle body positioned within the channel of the cover member to movably couple the cover member to the handle body.

8. The oral care implement according to claim 1 further comprising a head coupled to the distal end of the handle body, a plurality of tooth cleaning elements extending from a front surface of the head.

9. The oral care implement according to claim 1 wherein the cover member comprises the cap portion and a base portion, the base portion of the cover member formed of a hard plastic and the cap portion of the cover member formed of a thermoplastic elastomer.

10. The oral care implement according to claim 1 wherein the cover member is both rotationally and translationally coupled to the handle body.

11. An oral care implement comprising:
a handle body extending along a longitudinal axis from a proximal end to a distal end, a cavity formed into the handle body;
an oral care dispenser comprising a housing having a reservoir for containing an oral care material and an applicator fluidly coupled to the reservoir;
a cover member comprising a cap portion coupled to the proximal end of the handle body, the cap portion comprising a resilient valve that is self-biased into a closed state; and
wherein the oral care dispenser is at least partially disposed within the cavity of the handle body, the oral care dispenser movably coupled to the handle body so as to be alterable between: (1) a retracted position in which the cap portion of the cover member encloses the applicator and the resilient valve is in the closed state; and (2) an extended position in which the applicator of the oral care dispenser extends through the resilient valve and the resilient valve is in an open state.

12. The oral care implement according to claim 11 further comprising a plurality of slits formed into the cap portion of the cover member and extending radially from a central point, the plurality of slits creating a plurality of flaps in the cap portion of the cover member, the plurality of slits and the plurality of flaps collectively forming the resilient valve.

13. The oral care implement according to claim 12 wherein when the oral care dispenser is in the retracted position the resilient valve is self-biased into the closed state and adjacent flaps abut one another, and wherein when the oral care dispenser is in the extended position the plurality of flaps separate along the plurality of slits thereby forming a passageway through the cap portion of the cover member through which the applicator of the oral care dispenser extends.

14. The oral care implement according to claim 11 further comprising:
an elongated recess formed through the handle body;
a protuberance extending from an outer surface of the housing of the oral care dispenser; and
wherein the protuberance extends into and through the elongated recess to form a knob to facilitate moving the oral care dispenser between the retracted and extended positions.

15. The oral care implement according to claim 11 wherein at least a portion of the housing of the oral care dispenser is positioned within the cavity of the handle body in both the retracted and extended positions.

16. The oral care implement according to claim 11 wherein the applicator is non-movable relative to the handle body, at least a portion of the applicator of the oral care dispenser protruding from the proximal end of the handle body in both the retracted and extended positions.

17. An oral care implement comprising:
a handle body extending along a longitudinal axis from a proximal end to a distal end;
an applicator at the proximal end of the handle body, the applicator fluidly coupled to a reservoir containing an oral care material;
a cover member having a cap portion, the cap portion comprising a resilient valve that is self-biased into a closed state so as to enclose the applicator; and
wherein relative positioning between the applicator and the cover member can be altered between: (1) a storage state in which the cap portion of the cover member encloses the applicator and the resilient valve is in the closed state; and (2) an application state in which the applicator extends through the resilient valve and the resilient valve is in an open state.

18. The oral care implement according to claim 17 wherein the cover member is coupled to the handle body in both the storage and application states.

19. The oral care implement according to claim 17 wherein the cover member is movably coupled to the handle body to alter the relative positioning between the applicator and the cover member, the cover member being alterable between: (1) an extended position in which the cap portion of the cover member encloses the applicator and the resilient valve is in the closed state; and (2) a retracted position in which the applicator extends through the resilient valve and the resilient valve is in the open state.

20. The oral care implement according to claim 17 further comprising:
   an oral care dispenser comprising a housing and the applicator, the housing having the reservoir, the oral care dispenser at least partially disposed within a cavity of the handle body; and
   wherein the oral care dispenser is movably coupled to the handle body to alter the relative positioning between the applicator and the cover member, the oral care dispenser being alterable between: (1) a retracted position in which the cap portion of the cover member encloses the applicator and the resilient valve is in the closed state; and (2) an extended position in which the applicator of the oral care dispenser extends through the resilient valve and the resilient valve is in the open state.

* * * * *